US008067647B2

(12) United States Patent
Takeda et al.

(10) Patent No.: US 8,067,647 B2
(45) Date of Patent: Nov. 29, 2011

(54) METHOD FOR PRODUCING β-NITROSTYRENE COMPOUND

(75) Inventors: Masahiro Takeda, Toyonaka (JP); Hiroshi Kadono, Nishinomiya (JP); Kazuo Murakami, Kashiba (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 12/452,877

(22) PCT Filed: Jul. 28, 2008

(86) PCT No.: PCT/JP2008/063521
§ 371 (c)(1),
(2), (4) Date: Jan. 27, 2010

(87) PCT Pub. No.: WO2009/017091
PCT Pub. Date: Feb. 5, 2009

(65) Prior Publication Data
US 2010/0130795 A1    May 27, 2010

(30) Foreign Application Priority Data

Jul. 31, 2007  (JP) .................. 2007 199547

(51) Int. Cl.
*C07C 205/04*    (2006.01)
(52) U.S. Cl. .................................. 568/927
(58) Field of Classification Search .................. 568/927
See application file for complete search history.

(56) References Cited

U.S. PATENT DOCUMENTS

| 4,822,375 | A  | 4/1989 | Lang et al. |
| 6,121,279 | A  | 9/2000 | Gutterer |
| 2009/0137819 | A1 | 5/2009 | Yasuoka et al. |

FOREIGN PATENT DOCUMENTS

| GB | 1 449 540 | 9/1976 |
| JP | 62-42923 A | 2/1987 |
| JP | 3-81745 | 4/1991 |
| JP | 4-193850 A | 7/1992 |
| JP | 9-194457 A | 7/1997 |
| JP | 11-71348 A | 3/1999 |
| JP | 2001-510827 A | 8/2001 |
| JP | 2001-278702 A | 10/2001 |
| JP | 2002-241364 A | 8/2002 |
| JP | 2005-320346 A | 11/2005 |
| WO | WO 99/05113 A1 | 2/1999 |
| WO | WO 2007/066828 A1 | 6/2007 |

OTHER PUBLICATIONS

Bourguignon et al., "Synthese d'Aryl nitronorbornenes par cycloaddtion de Diels-Alder entre les aryl-nitroethylenes et le cyclopentadiene. Justification de la stereochimie et de la reactivite realtive observees par la methode CNDO-II. Obtention d'aryl aminonorbornenes.", Canadian Journal of Chemistry, 1985, 63(9):2354-2361.
Latif, et al. "N-Unsubstituted (Carbamoyloxy)nitrostyrenes: A New Series of Aryl-B-nitroalkenes with Fungicidal Properties", Liebigs Ann. Chem., 1987, pp. 495-498.
Latif, et al. "Reaction of Biologically Active B-Nitrostyrenes with o-Phenylenediamine: A New Route to the Synthesis of 2-Substituted Benzimidazoles" Indian Journal of Chemistry, Sep. 1982, vol. 21B, pp. 872-874.
Supplementary EP Search Report in EP Appln No. 08 79 1756 dated Dec. 30, 2010.
International Search Report received in corresponding International Application No. PCT/JP2008/063521 (2 pgs.), Aug. 26, 2008.
Gabriel Vallejos et al., "Heteroarylisopropylamines as MAO Inhibitors", Bioorganic & Medicinal Chemistry, 2005, vol. 13, No. 14, pp. 4450-4457.
Lakshmi Kant Bajpai et al., "Unusual Denitrohydrogenation of Allylic Tertiary Nitro Compounds During Hydrogenation", Synthetic Communications, 1995, vol. 25, No. 12, pp. 1765-1775.
Tomotaka Okino et al., "Enantio- and Diastereoselective Michael Reaction of 1,3-Dicarbonyl Compounds to Nitroolefins Catalyzed by a Bifunctional Thiourea", J. Am. Chem. Soc. 2005, vol. 127, pp. 119-125.

*Primary Examiner* — Sikarl Witherspoon
(74) *Attorney, Agent, or Firm* — Foley & Lardner LLP

(57) ABSTRACT

A method for producing a β-nitrostyrene compound is provided in which a benzaldehyde derivative represented by the following formula (I):

[Chemical Formula 1]

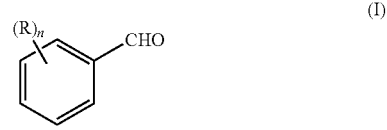

(I)

and nitromethane are condensed in an acetic acid solvent in the presence of a primary amine. This method allows production of a β-nitrostyrene compound at a high yield in the industrially-safe reaction temperature range.

6 Claims, No Drawings

METHOD FOR PRODUCING β-NITROSTYRENE COMPOUND

TECHNICAL FIELD

The present invention relates to a method for producing a β-nitrostyrene compound useful as a medicinal intermediate.

BACKGROUND ART

The β-nitrostyrene compound represented by the following formula is a useful intermediate for producing a therapeutic drug for treating reflux esophagitis, an antispasmodic and the like, such as baclofen.

[Chemical Formula 1]

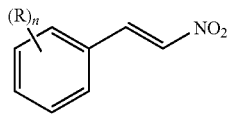

(in the above formula, n represents an integer of 0 to 3, and n Rs may be identical or different and each may represent a halogen atom, an alkyl group, a hydroxyl group, an alkoxy group, a haloalkyl group, or a cycloalkyloxy group, or when n represents 2 or 3, two Rs may together form an alkylenedioxy group.)

Some of the methods for synthesizing such a β-nitrostyrene compound are conventionally known. For example, Japanese Patent Laying-Open No. 09-194457 (Patent Document 1), Japanese Patent Laying-Open No. 11-71348 (Patent Document 2), Japanese Patent National Publication No. 2001-510827 (Patent Document 3), and the like disclose the method for synthesizing a β-nitrostyrene compound by the heating and refluxing process using ammonium acetate as a base. However, in the case where ammonium acetate is used in this way, the reaction temperature is required to be set at a temperature close to its boiling point.

Furthermore, for example, the method disclosed in each of Japanese Patent Laying-Open No. 2002-241364 (Patent Document 4) and J. Am. Chem. Soc. (2005, 127, 119-125) (Non-Patent Document 1) is also known as a method for synthesizing a β-nitrostyrene compound. For example, Patent Document 1 discloses that a β-nitrostyrene compound can be produced at a yield of 67% under reflux conditions by using nitroalkane as a solvent and benzylamine as a base. However, also in this method, a reaction occurs at the heating temperature close to its boiling point.

Since the β-nitrostyrene compound is produced by the reaction using a nitro compound, it is feared that the reaction may, for example, get out of control. Thus, the reaction occurring at the heating temperature close to the boiling point may cause a problem in practical implementation from an industrial point of view. For example, when the β-nitrostyrene compound is actually produced, the residence time of the reaction solution of nitromethane and benzaldehyde is about 12 hours. As for the reaction solution of nitromethane and benzaldehyde, when the operating temperature is at 95° C., the time taken for the velocity of the self reaction in the adiabatic system to reach its maximum value (excursion) is 7.9 hours according to the measurement by an accelerating rate calorimeter (ARC).

Consequently, there is a need to provide a method for producing a β-nitrostyrene compound at a high yield by the reaction of nitromethane and benzaldehyde in the temperature range which is regarded as safe from an industrial point of view.

Patent Document 1: Japanese Patent Laying-Open No. 09-194457
Patent Document 2: Japanese Patent Laying-Open No. 11-71348
Patent Document 3: Japanese Patent National Publication No. 2001-510827
Patent Document 4: Japanese Patent Laying-Open No. 2002-241364
Non-Patent Document 1: J. Am. Chem. Soc. 2005, 127, 119-125

DISCLOSURE OF THE INVENTION

Problems to be Solved by the Invention

The present invention has been made to solve the above-described problems, and an object of the present invention is to provide a method by which a β-nitrostyrene compound can be produced at a high yield in the industrially-safe reaction temperature range.

Means for Solving the Problems

The present inventors have made an earnest study in order to solve the above-described problems, and have completed the present invention by finding that a β-nitrostyrene compound can be produced at a high yield in the presence of a primary amine by condensing a benzaldehyde derivative represented by the following formula (I):

[Chemical Formula 2]

(I)

(in formula (I), n represents an integer of 0 to 3, and n Rs may be identical or different and each may represent a halogen atom, an alkyl group, a hydroxyl group, an alkoxy group, a haloalkyl group, or a cycloalkyloxy group, or when n represents 2 or 3, two Rs may together form an alkylenedioxy group) and nitromethane in an acetic acid solvent in a presence of a primary amine. The β-nitrostyrene compound is represented by the following formula (II):

[Chemical Formula 3]

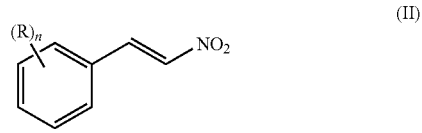

(II)

(in formula (II), n and R are as set forth above). In other words, the present invention is as described below.

The present invention provides a method for producing a β-nitrostyrene compound, characterized by condensing a benzaldehyde derivative represented by the following formula (I):

[Chemical Formula 4]

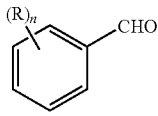
(I)

(in formula (I), n represents an integer of 0 to 3, and n Rs may be identical or different and each may represent a halogen atom, an alkyl group, a hydroxyl group, an alkoxy group, a haloalkyl group, and a cycloalkyloxy group, or when n represents 2 or 3, two Rs may together form an alkylenedioxy group) and nitromethane in an acetic acid solvent in the presence of a primary amine. The β-nitrostyrene compound is represented by the following formula (II):

[Chemical Formula 5]

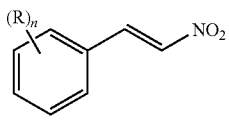
(II)

(in formula (II), n and R are as set forth above).

In the method for producing a β-nitrostyrene compound according to the present invention, it is preferable that the primary amine is benzylamine.

In the method for producing a β-nitrostyrene compound according to the present invention, it is preferable that a reaction temperature is 70 to 80° C.

In the method for producing a β-nitrostyrene compound according to the present invention, it is preferable that the benzaldehyde derivative represented by the above formula (I) is 4-chlorobenzaldehyde and the β-nitrostyrene compound represented by the above formula (II) is 4-chloro-β-nitrostyrene.

In the method for producing a β-nitrostyrene compound according to the present invention, it is preferable that an amount of the primary amine (preferably, benzylamine) used is equivalent to 0.2 to 1.5-fold molar amount with respect to 1 mol of benzaldehyde.

EFFECTS OF THE INVENTION

According to the present invention, a β-nitrostyrene compound can be produced at a high yield in the industrially-safe reaction temperature range.

BEST MODES FOR CARRYING OUT THE INVENTION

In the method for producing a β-nitrostyrene compound according to the present invention, a benzaldehyde derivative represented by the following formula (I) is used as raw material.

[Chemical Formula 6]

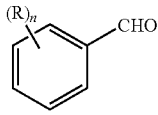
(I)

In the above formula (I), n represents an integer of 0 to 3, preferably an integer of 0 to 2. Furthermore, in the above formula (I), n Rs may be identical or different and each may represent a halogen atom, an alkyl group, a hydroxyl group, an alkoxy group, a haloalkyl group, or a cycloalkyloxy group, or when n represents 2 or 3, two Rs may together form an alkylenedioxy group.

The halogen atom in the benzaldehyde derivative used in the present invention includes a fluorine atom, a chloro atom, a bromine atom, and an iodine atom.

The alkyl group in the benzaldehyde derivative used in the present invention includes, for example, a linear or branched lower alkyl group having 1 to 6 carbons, and specifically includes a methyl group, an ethyl group, a propyl group, an isopropyl group, an n-butyl group, an isobutyl group, a sec-butyl group, a tert-butyl group, an n-pentyl group, an isopentyl group, a tert-pentyl group, a neopentyl group, an n-hexyl group, an isohexyl group, a 3-methyl pentyl group, a neohexyl group, a 2,3-dimethyl butyl group, and the like.

The alkoxy group in the benzaldehyde derivative used in the present invention includes, for example, an alkoxy group having 1 to 3 carbons, and specifically includes a methoxy group, an ethoxy group, a propoxy group, and the like.

The haloalkyl group in the benzaldehyde derivative used in the present invention includes, for example, a haloalkyl group having 1 to 3 carbons, and specifically includes a fluoromethyl group, a trifluoromethyl group, and the like.

The cycloalkyloxy group in the benzaldehyde derivative used in the present invention includes, for example, a cycloalkyloxy group having 3 to 6 carbons, and specifically includes a cyclopropoxy group, a cyclopentyloxy group, and the like.

A chloro atom is preferable among these substituents, and 4-chlorobenzaldehyde is preferable as a benzaldehyde derivative represented by the above formula (I).

The method for producing a β-nitrostyrene compound according to the present invention is characterized by the condensation reaction of the benzaldehyde derivative as described above with nitromethane in the presence of a primary amine in the acetic acid solvent. In this case, acetic acid is used as a solvent because it may facilitate crystallization of the β-nitrostyrene compound (which will be described later) by addition of water as a post treatment of the reaction, in contrast to toluene and the like generally used as a solvent.

The used amount of acetic acid as a solvent is usually 4 to 8 times by weight, preferably 5 to 6 times by weight, with respect to 1 part by weight of the benzaldehyde derivative. This is because the used amount of acetic acid is less than 4 times by weight with respect to 1 part by weight of the benzaldehyde derivative, which may cause an increase in the viscosity of the reaction solution to thereby make it difficult to perform stirring; and also because the used amount of acetic acid exceeds 8 times by weight with respect to 1 part by weight of the benzaldehyde derivative, which may cause a decrease in volumetric efficiency and this is uneconomical.

The used amount of nitromethane is usually 1 to 10-fold molar amount, preferably 3 to 5-fold molar amount, with respect to 1 mol of the benzaldehyde derivative. This is because, in the case where the used amount of nitromethane is less than 1-fold molar amount with respect to 1 mol of the benzaldehyde derivative, the yield may decrease; and also because, in the case where the used amount of nitromethane exceeds 10-fold molar amount with respect to 1 mol of the benzaldehyde derivative, sufficient effects corresponding to the used amount cannot be achieved, which is uneconomical.

The primary amine used in the method for producing a β-nitrostyrene compound according to the present invention includes, for example, ethylamine, n-propylamine, isopropylamine, 2-aminoethanol, 3-aminoethanol, benzylamine, and the like. Among others, n-propylamine, 2-aminoethanol or benzylamine is preferable, and benzylamine is particularly preferable.

The used amount of the primary amine is usually 0.2 to 1.5-fold molar amount, preferably 0.2 to 1.0-fold molar amount, with respect to 1 mol of the benzaldehyde derivative. This is because, in the case where the used amount of the primary amine is less than 0.2-fold molar amount with respect to 1 mol of the benzaldehyde derivative, the reaction velocity may decrease; and also because, in the case where the used amount of the primary amine exceeds 1.5-fold molar amount with respect to 1 mol of the benzaldehyde derivative, sufficient effects corresponding to the used amount cannot be achieved, which is uneconomical.

The method of adding a benzaldehyde derivative and a primary amine to acetic acid and dripping nitromethane at the reaction temperature is preferable as a reaction method from a safety point of view. The temperature at which nitromethane is dripped is usually 30 to 80° C., preferably 70 to 80° C. The time period during which nitromethane is dripped is usually 30 minutes to 6 hours, preferably 1 to 3 hours, though it depends on the used amount and the temperature at which nitromethane is dripped.

The reaction temperature is usually 30 to 80° C., preferably 70 to 80° C. This is because the reaction velocity may be decreased in the case where the reaction temperature is less than 30° C.; and also because control of the reaction may be difficult in the case where the reaction temperature exceeds 80° C.

The reaction time is usually 10 minutes to 6 hours though it varies depending on the used amount of raw materials, the reaction temperature, and the like.

According to the method for producing a β-nitrostyrene compound of the present invention, ADT24 (Adiabatic Decomposition Temperature for 24 hrs: the temperature index obtained in terms of the fact that the time period of 24 hours is sufficient to allow treatment such as cooling to be performed even when the reaction tends to get out of control) which represents an index of the temperature for safely operation can be set at 78° C. At this temperature or below, the reaction can be prevented from getting out of control for 24 hours under heat insulating conditions. It is to be noted that ADT24 can be measured by an accelerating rate calorimeter (ARC) (made by CSI corporation). Thus, the present invention can provide a method by which a β-nitrostyrene compound can be produced in the industrially-safe reaction temperature range.

By the reaction as described above, a β-nitrostyrene compound represented by the following formula (II) is produced.

[Chemical Formula 7]

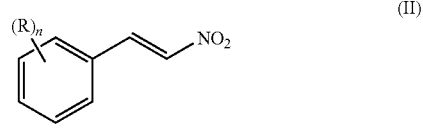

(II)

In the above formula (II), n and R are as set forth above with regard to the above formula (I). Furthermore, as described above, 4-chlorobenzaldehyde is preferable as a benzylamine derivative, and accordingly, 4-chloro-β-nitrostyrene is preferable as a β-nitrostyrene compound.

The method for producing a β-nitrostyrene compound according to the present invention is not only industrially safe as described above, but also allows production of a β-nitrostyrene compound at a yield such as 80 to 99% (suitably, 85 to 98%) which is remarkably higher than in the conventional case, even when the reaction occurs in the industrially-safe reaction temperature range.

As a post treatment after the reaction, water is dripped into the reaction solution, for example, at 30 to 60° C., or the reaction solution is dripped into water, which allows crystallization of the β-nitrostyrene compound generated by the reaction.

Although the present invention will be described in further detail with reference to Examples and Comparative Examples, the present invention is not limited thereto.

EXAMPLE 1

First, 200.14 grams (1.356 mol) of 4-chlorobenzaldehyde and 153.4 grams (1.429 mol) of benzylamine were added to 1066.8 grams of acetic acid and dissolved therein. This solution was heated to a temperature of 78° C. Then, 325.7 grams (5.336 mol) of nitromethane was dripped into the solution at 78 to 80° C. for 2 hours and 50 minutes, and the resultant solution was stirred at about 79° C. for 40 minutes. Then, 1016 grams of water was dripped into the solution at about 50° C. for 2 hours and 25 minutes. The resultant solution was cooled to about 10° C. for 1 hour and 50 minutes and stirred at 6 to 10° C. for 1 hour and 50 minutes. The solution was filtered to remove crystals which were then washed with 1016.2 grams of water. The wet crystals were dissolved at about 50° C. in 572.8 grams of toluene, which was then subjected to liquid separation to remove a water phase, and washed with 330.8 grams of water. As a result of analyzing the toluene layer (803.24 grams), 253.8 grams of 4-chloro-β-nitrostyrene was contained and the yield thereof was 97.1%.

EXAMPLE 2

When 0.5-fold molar amount of benzylamine with respect to 1 mol of 4-chlorobenzaldehyde was used and reacted as in Example 1, the production ratio of 4-chloro-β-nitrostyrene was 95% after two hours since the reaction. The production ratio was measured by high-performance liquid chromatography (hereinafter the same shall apply).

EXAMPLE 3

When 0.2-fold molar amount of benzylamine with respect to 1 mol of 4-chlorobenzaldehyde was used and reacted as in Example 1, the production ratio of 4-chloro-β-nitrostyrene was 82% after eight hours since the reaction.

EXAMPLE 4

When 0.5-fold molar amount of n-propylamine with respect to 1 mol of 4-chlorobenzaldehyde was used and reacted as in Example 1, the production ratio of 4-chloro-β-nitrostyrene was 80.3% after six hours since the reaction.

EXAMPLE 5

When 1.0-fold molar amount of n-propylamine with respect to 1 mol of 4-chlorobenzaldehyde was used and reacted as in Example 1, the production ratio of 4-chloro-β-nitrostyrene was 84.2% after two hours since the reaction.

EXAMPLE 6

When 0.5-fold molar amount of 2-aminoethanol with respect to 1 mol of 4-chlorobenzaldehyde was used and reacted as in Example 1, the production ratio of 4-chloro-β-nitrostyrene was 86.0% after five hours since the reaction.

EXAMPLE 7

When 1.0-fold molar amount of 2-aminoethanol with respect to 1 mol of 4-chlorobenzaldehyde was used and reacted as in Example 1, the production ratio of 4-chloro-β-nitrostyrene was 84.4% after two hours since the reaction.

COMPARATIVE EXAMPLE 1

First, 100 grams (0.711 mol) of 4-chlorobenzaldehyde and 95.4 grams (1.238 mol) of ammonium acetate were added to 750 ml of acetic acid, to which 227.7 grams (3.56 mol) of nitromethane was added and stirred at 79.2 to 79.9° C. for 6 hours (the reaction ratio was 62% after three hours and 70% after six hours). The resultant solution was left to stand still at about 60° C. overnight, and then, 750 grams of water was dripped into the solution at about 58° C. for 2 hours.

The solution was cooled to about 10° C. for 40 minutes and stirred for one hour. The resultant solution was filtered to remove crystals, which were then washed with 375 grams of water. The wet crystals were added to 730 ml of toluene and dissolved therein at about 50° C. The resultant solution was then subjected to liquid separation to remove a water phase, and washed with 165 grams of water. As a result of analyzing the toluene layer (722.1 grams), 105.8 grams of 4-chloro-β-nitrostyrene was contained and the yield thereof was 81%.

COMPARATIVE EXAMPLE 2

When 0.2-fold molar amount of ammonium acetate with respect to 1 mol of 4-chlorobenzaldehyde was used and reacted as in Comparative Example 1, the production ratio of 4-chloro-β-nitrostyrene was 40% after eight hours since the reaction.

It should be understood that the embodiments, examples and comparative examples disclosed herein are illustrative and non-restrictive in every respect. The scope of the present invention is defined by the terms of the claims, rather than the description above, and is intended to include any modifications within the scope and meaning equivalent to the terms of the claims.

The invention claimed is:

1. A method for producing a β-nitrostyrene compound by condensing a benzaldehyde derivative represented by the following formula (I):

[Chemical Formula 1]

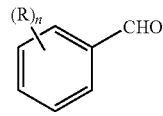

(I)

(in formula (I), n represents an integer of 0 to 3, and n Rs may be identical or different and each may represent a halogen atom, an alkyl group, a hydroxyl group, an alkoxy group, a haloalkyl group, or a cycloalkyloxy group, or when n represents 2 or 3, two Rs may together form an alkylenedioxy group) and nitromethane in an acetic acid solvent in a presence of a primary amine, said β-nitrostyrene compound being represented by the following formula (II):

[Chemical Formula 2]

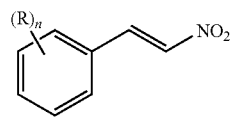

(II)

(in formula (II), n and R are as set forth above),
wherein said condensing is performed at a reaction temperature of 30 to 80° C.

2. The method for producing a β-nitrostyrene compound according to claim 1, wherein the primary amine is benzylamine.

3. The method for producing a β-nitrostyrene compound according to claim 2, wherein an amount of benzylamine used is equivalent to 0.2 to 1.5-fold molar amount with respect to 1 mol of benzaldehyde.

4. The method for producing a β-nitrostyrene compound according to claim 1, wherein a reaction temperature is 70 to 80° C.

5. The method for producing a β-nitrostyrene compound according to claim 1, wherein the benzaldehyde derivative represented by said formula (I) is 4-chlorobenzaldehyde and the β-nitrostyrene compound represented by said formula (II) is 4-chloro-β-nitrostyrene.

6. The method for producing a β-nitrostyrene compound according to claim 1, wherein an amount of primary amine used is equivalent to 0.2 to 1.5-fold molar amount with respect to 1 mol of benzaldehyde.

* * * * *